(12) United States Patent
Dougherty, Sr.

(10) Patent No.: US 11,904,044 B1
(45) Date of Patent: Feb. 20, 2024

(54) BRUISE REMOVAL CREAM

(71) Applicant: Franklin Wayne Dougherty, Sr., Cypress, TX (US)

(72) Inventor: Franklin Wayne Dougherty, Sr., Cypress, TX (US)

( * ) Notice: Subject to any disclaimer, the term of this patent is extended or adjusted under 35 U.S.C. 154(b) by 0 days.

(21) Appl. No.: 18/316,759

(22) Filed: May 12, 2023

(51) Int. Cl.
*A61Q 19/00* (2006.01)
*A61K 8/9794* (2017.01)
*A61K 8/9789* (2017.01)

(52) U.S. Cl.
CPC .......... *A61K 8/9794* (2017.08); *A61K 8/9789* (2017.08); *A61Q 19/00* (2013.01)

(58) Field of Classification Search
CPC .................................................... A61Q 19/00
See application file for complete search history.

(56) References Cited

FOREIGN PATENT DOCUMENTS

CN 114869788 A * 8/2022

* cited by examiner

*Primary Examiner* — Qiuwen Mi
(74) *Attorney, Agent, or Firm* — Law Office of Jeff Williams PLLC; J. Oliver Williams

(57) ABSTRACT

A bruise removal cream includes a combination of coconut oil, salt, and mullein garlic. The cream is mixed in accordance with predetermined ratios by weight and is selectively heated to ensure the dissolving of the salt. A method of application of the bruise removal cream to the surface of the base skin is provided. Application includes rubbing the cream onto the surface of the bruise. The cream should be applied upwards of four times daily.

10 Claims, 1 Drawing Sheet

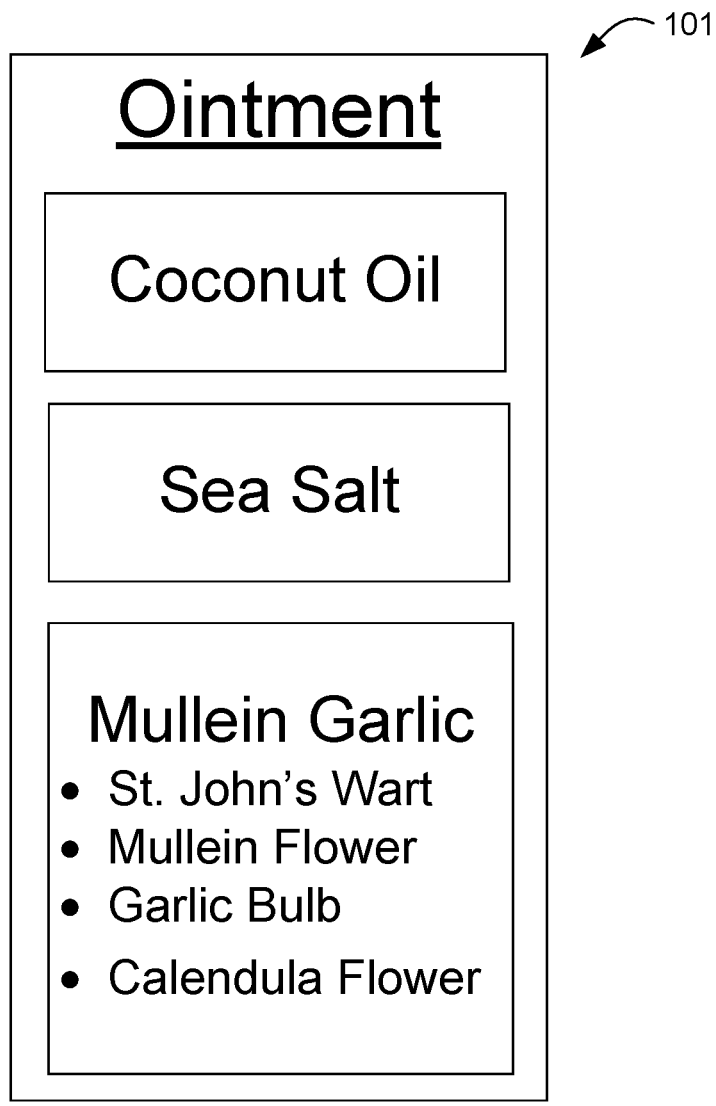

BRUISE REMOVAL CREAM

BACKGROUND OF THE INVENTION

1. Field of the Invention

The present application relates to a cream or ointment used in their treatment of bruises.

2. Description of Related Art

The medical term for a bruise is an ecchymosis. Bruises are formed when small blood vessels near the surface of the skin are broken from an impact or injury. Blood leaks from the vessels and causes a discoloration around the impact area. These often appear as a dark mark on the skin. Bruises are not uncommon and are often unsightly in appearance to the average user.

Various methods have been used to try and remove the effects of a bruise some methods involve ice therapy where ice is applied immediately after the impact or injury so as to reduce blood flow to the area. Other methods include heat where you can apply heat to the area so as to boost the circulation and increase blood flow. Other methods also include compression where the bruised area is wrapped in a bandage so as to minimize blood flow to the area. Likewise another method to remove blood flow to the area is through elevation of the appendage where the bruise occurred.

It is also understood that various ointments or natural elements have been attempted via a topical Application on the skin. Commonly these include vitamin K cream, aloe vera, vitamin C, pineapple, and even comfrey. Bruises may take weeks to heal. The use of various remedies can assist in speeding up the healing process and removing discoloration. Despite these remedies it may still take upwards of a week or more for a bruise to be remove visually from the skin.

Although strides have been made, shortcomings remain. It is desired that an ointment or cream be provided which speeds up the process of bruise removal.

BRIEF SUMMARY OF THE INVENTION

It is an object of the present application to provide an ointment or cream configured to accelerate the removal of a bruise from the skin period it is a further object of the present application that the ingredients for the ointment or cream being natural elements. the ingredients are mixed according to a specific ratio and are applied topically to the skin around the area impact or injury. A gentle application or pressure or rubbing on the impact area may be performed to assist in working the ointment or cream into the skin.

Ultimately the invention may take many embodiments. In these ways, the present invention overcomes the disadvantages inherent in the prior art. The more important features have thus been outlined in order that the more detailed description that follows may be better understood and to ensure that the present contribution to the art is appreciated. Additional features will be described hereinafter and will form the subject matter of the claims that follow.

Many objects of the present application will appear from the following description and appended claims, reference being made to the accompanying drawings forming a part of this specification wherein like reference characters designate corresponding parts in the several views.

Before explaining at least one embodiment of the present invention in detail, it is to be understood that the embodiments are not limited in its application to the details of construction and the arrangements of the components set forth in the following description or illustrated in the drawings. The embodiments are capable of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the various purposes of the present design. It is important, therefore, that the claims be regarded as including such equivalent constructions insofar as they do not depart from the spirit and scope of the present application.

BRIEF DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

FIG. 1 is a chart of a representative ointment or bruise removal cream according to an embodiment of the present application.

While the embodiments and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE INVENTION

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the embodiments described herein may be oriented in any desired direction.

The cream and method of application in accordance with the present application overcomes one or more of the above-discussed problems commonly associated with the prior art discussed previously. In particular, the cream is made from natural products including which is mullein garlic. The cream is administered A plurality of times a day and may be gently rubbed into the surface of the skin. These and other unique features are discussed below and illustrated in the accompanying drawings.

The embodiments and method will be understood, both as to its structure and operation, from the accompanying drawings, taken in conjunction with the accompanying description. Several embodiments of the assembly may be presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless otherwise described.

Referring now to the FIGURES wherein like reference characters identify corresponding or similar elements in form and function throughout the several views. The following FIGURES describe embodiments of the present application and its associated features. With reference now to the FIGURES, embodiments of the present application are herein described. It should be noted that the articles "a", "an", and "the", as used in this specification, include plural referents unless the content clearly dictates otherwise.

Referring now to FIG. 1 in the drawings, a chart representing the ingredients of the bruise removal cream 101 is illustrated. Mullein is an herb that has been known to have medicinal purposes and properties. It has been used in different ways and for the purpose of soothing inflamed and irritated nerves as well as relieving pain to a user. It is understood to have antimicrobial properties and has antiviral actions which result in the ability of it being used to fight off infections. It can be mixed with different natural elements such as garlic. The use of garlic with mullein helps to increase the antiviral and antimicrobial characteristics of each element.

Cream 101 includes A plurality of ingredients that are mixed together in accordance with a particular ratio. At least three of the ingredients include coconut oil, sea salt, and mullein garlic. Mullein garlic maybe provided or used in different physical forms. Mullein garlic may be found in an oil configuration or via a more solid configuration. Mullein garlic is mixed with the coconut oil and the sea salt to product the bruise removal cream 101 of the present application.

Mullein garlic maybe form from a proprietary blend of different extracts. One such blend may include the following: St. John's wart flowering top (*Hypericum* Perf.), Mullein flower (*Verbascum*), garlic bulb (*allium sativum*), and Calendula Flower (*Calendula Officinalis*.). These four ingredients are included in accordance with a proprietary blend and proportioned to make up mullein garlic.

Bruise removal cream 101 is made in the following manner. One quarter cup of coconut oil is placed into a container. The coconut oil may be organic in nature. One teaspoon (tsp) of salt is added to the coconut oil. The combination is then heated for a period of time, such as 10 to 20 seconds, in an effort to more liquify this solution. A common method of heating the oil and salt may be through the use of a microwave. It is also understood that upwards of 17 to 20 seconds is an ideal time frame to heat the solution, but the time of heating is dependent upon the amount of energy applied. Once heated, the coconut oil and salt solution is removed and stirred until the salt is fully dissolved. next, mullein garlic oil is added to the oil solution in the amount of 0.84 ounces.

It is understood that the quantities of ingredients by weight may vary slightly. And exemplary solution may include the following weights of ingredients: 2.36 ounces of coconut oil, 17 ounces of salt, 0.63 ounces of mullein garlic. as seen with these two descriptions a bruise removal cream 101, a weight range of mullein garlic added to a combination of salt and coconut oil solution maybe in amounts of 0.6 ounces upwards to ounces. It is also understood that the potency of bruise removal cream 101 may also be influenced by the proprietary blend of the mullein garlic oil that is used with its 4 main ingredients. A general rule of thumb is that the weight of mullein garlic is less than 40% that of the weight of coconut oil.

In application, a user withdraws an amount of cream 101 and applies it topically to the skin three to five times a day, ideally four times daily should be sufficient. the user gently rubs or massages cream 101 on the surface of the skin for a time period between seconds to one minute. The act of rubbing or massaging the cream 101 onto the surface of the skin aids in absorption and enhances the effect. Bruise removal cream 101 is configured to immediately affect the treatment area with visual reduction in the bruise beginning as early as one day after treatment begins. In most cases the bruise may be gone within one week when treatment is maintained consistently.

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A bruise removal cream, comprising:
a volume of coconut oil;
a volume of salt; and
a volume of mullein garlic;
where in the mullein garlic is mixed within a heated solution of the coconut oil and salt mixture.

2. The bruise removal cream of claim 1, wherein the mullein garlic includes at least St. John's wart flowering top, mullein flour, garlic bulb, and calendula flower.

3. The bruise removal cream of claim 1, wherein the amount of mullein garlic by weight is less than 40% of the weight of the coconut oil.

4. The bruise removal cream of claim 1 wherein the volume of salt is weighted at ounces.

5. The bruise removal cream of claim 1 wherein the volume of coconut oil is weighted at 2.36 ounces.

6. The bruise removal cream of claim 1 wherein the volume of mullein garlic is weighted at 0.63 ounces.

7. The bruise removal cream of claim 1 where in the volume of coconut oil is weighted at 2.63 oz, the volume of salt is weighted at 0.17 ounces, and the volume of mullein garlic is weighted at 0.63 ounces.

8. A method of removing a bruise from skin, comprising:
   obtaining a bruise removal cream in claim 1;
   applying the bruise removal cream to a surface of the skin; and
   rubbing the bruise removal cream onto the surface of the skin.

9. The method of claim 8, wherein the act of rubbing the bruise removal cream onto the surface of the skin persists between 30 seconds and one minute.

10. The method of claim 8, wherein in the bruise removal cream is applied four times daily to the surface of the skin.

\* \* \* \* \*